United States Patent [19]

Reinhardt, III

[11] 4,225,519
[45] Sep. 30, 1980

[54] DEHYDROCHLORINATION PROCESS

[75] Inventor: Arthur E. Reinhardt, III, Corpus Christi, Tex.

[73] Assignee: PPG Industries, Inc., Pittsburgh, Pa.

[21] Appl. No.: 970,674

[22] Filed: Dec. 18, 1978

Related U.S. Application Data

[62] Division of Ser. No. 852,897, Nov. 18, 1977, Pat. No. 4,144,192.

[51] Int. Cl.$^2$ .................................................. C07C 17/34
[52] U.S. Cl. .................................. 260/654 D; 252/438; 252/451
[58] Field of Search ................... 260/654 D; 252/438

[56] References Cited

U.S. PATENT DOCUMENTS

| | | | |
|---|---|---|---|
| 2,696,497 | 12/1954 | Cines | 260/500 |
| 2,803,678 | 8/1957 | Conrad | 260/654 D |
| 2,927,903 | 3/1960 | Nixon | 252/466 |
| 3,214,419 | 10/1965 | Hodgdon | 260/89.7 |
| 3,313,739 | 4/1967 | Acker | 252/431 |
| 3,398,131 | 8/1968 | Bloch et al. | 260/94.9 |
| 3,760,015 | 9/1973 | Berkowitz | 260/654 D |
| 3,869,520 | 3/1975 | Gordon | 260/654 D |
| 3,870,762 | 3/1975 | Stacey et al. | 260/654 D |
| 3,927,131 | 12/1975 | Ward | 260/654 D |
| 3,996,338 | 12/1976 | Frampton | 423/335 |
| 4,076,651 | 2/1978 | Jacques | 252/431 |

Primary Examiner—Arthur P. Demers
Attorney, Agent, or Firm—Edward J. Whitfield

[57] ABSTRACT

Increased selectivity to vinylidene chloride is obtained in the catalytic vapor phase dehydrochlorination of 1,1,2-trichloroethane by conducting the reaction in the presence of a cesium nitrate catalyst.

6 Claims, No Drawings

DEHYDROCHLORINATION PROCESS

This is a division of application Ser. No. 852,897, filed Nov. 18, 1977 now U.S. Pat. No. 4,144,192.

BACKGROUND OF THE INVENTION

It is known to crack or thermally dehydrochlorinate 1,1,2-trichloroethane to obtain 1,1-dichloroethylene (vinylidene chloride) and an isomeric mixture of cis- and trans-1,2-dichloroethylenes. Vinylidene chloride may be either polymerized to produce polyvinylidene chloride resin or may be catalytically hydrochlorinated to produce methylchloroform, a commonly used degreasing solvent. Since the 1,2-dichloroethylene isomers are of considerably less value, the vapor phase reaction is typically conducted in the presence of catalysts which selectively favor the formation of vinylidene chloride.

U.S. Pat. No. 3,870,762 discloses dehydrochlorinating 1,1,2-trichloroethane in the presence of a chloride or fluoride of potassium, cesium or rubidium carried on a silica support of a type known as Porasil ®. Copending, commonly assigned application Ser. No. 744,564, filed Nov. 24, 1976, discloses a vinylidene chloride selective catalyst comprising cesium halide, preferably cesium chloride, supported on humidified, high surface area silica gel.

A catalyst has been found which gives improved selectivity to vinylidene chloride in the vapor phase dehydrochlorination of 1,1,2-trichloroethane, especially when the vapor phase reaction is conducted at super-atmospheric pressure.

SUMMARY OF THE INVENTION 1,1,2-Trichloroethane is dehydrochlorinated in the vapor phase in the presence of a catalyst comprising cesium nitrate and more particularly cesium nitrate supported on humidified, regular density silica gel.

DESCRIPTION OF THE INVENTION

Generally, the catalyst of the invention is prepared by contacting humidified, regular density silica gel with a cesium nitrate solution and drying the cesium nitrate impregnated silica gel.

The term "silica gel" generically includes a wide variety of materials having a wide range of physical properties and compositional limits. As used herein, "silica gel" refers specifically to amorphous, regular density silica gel having a high surface area. More particularly, the silica gel for use in accordance with the invention has a BET surface area of at least 500 and typically between 600 and 800 square meters per gram, an average pore diameter of between 10 and 100 angstroms and a silica ($SiO_2$) content of at least 99.5 percent of weight on an anhydrous basis. The silica gel usually contains trace amounts of metal oxides, such as aluminum, iron and sodium oxides, in amounts usually not in excess of about 0.2 percent by weight on an anhydrous basis. The bound water content of the silica gel (which is substantially equivalent to the loss on ignition at 950° C.) is in the range of 5 to 14 percent by weight.

Silica gel, when contacted with liquid water or lower alkyl alcohols readily disintegrates into small particles often with the rapid evolution of heat. Due to this disintegration, it is difficult to prepare a catalyst support of a predictable size by contacting the silica gel with an aqueous solution of the catalytically active material. To prevent disintegration when contacted with an aqueous solution of the catalytically active material (in this instance, cesium nitrate), the silica gel is first subjected to a humidification treatment.

Humidification is effected by exposing the silica gel to water vapor, preferably by contacting the silica gel with a gas such as air or nitrogen saturated with water vapor. The humidification temperature is not particularly critical, however, the temperature should not be so low as to result in ice formation or so high as to tend to desorb moisture from the silica gel. Preferably, humidification is effected at a temperature of between 5° C. and 50° C.

The adsorption by the silica gel of water vapor from the saturated carrier gas is gradual with no apparent exothermicity such as is observed when the silica gel is contacted with liquid water. Depending on conditions, the silica gel may be sufficiently humidified in as little as one hour or as long as one month. Although to effect humidification it is sufficient to simply expose the silica gel to water vapor laden carrier gas at atmospheric pressure, humidification may be effected more rapidly by passing the vapor laden carrier gas under pressure through a bed of silica gel.

The degree of humidification will vary depending on the precise composition and physical properties of the silica gel, however, a simple test determines when the silica gel is sufficiently humidified, i.e., a sample of the silica gel is contacted with liquid water at ambient temperature, and if there is no significant disintegration, the silica gel is adequately humidified.

After the silica gel has been humidified, it is contacted with an aqueous solution of cesium nitrate at such concentration and for a time sufficient to impregnate the silica gel with the desired quantity of cesium nitrate. The cesium nitrate impregnated silica gel is then dried to remove excess moisture and is ready for use. Although the cesium nitrate content of the catalyst is not particularly critical, generally useful levels for vapor phase dehydrochlorination are in the range of 0.5 to 25 percent and preferably between 5 to 15 percent and most preferably about 10 percent by weight cesium nitrate based on the combined weight of cesium nitrate and silica gel.

In a typical practice of the invention, 1,1,2-trichloroethane is dehydrochlorinated in the vapor phase by contacting a vaporous feed of 1,1,2-trichloroethane with a catalyst comprising cesium nitrate supported on humidified, regular density silica gel. The dehydrochlorination is conducted at elevated temperature, at atmospheric or super-atmospheric pressure and for a time sufficient to effect the desired degree of conversion of 1,1,2-trichloroethane. Dehydrochlorination in accordance with this invention is preferably conducted in accordance with the process described in copending, commonly assigned application Ser. No. 948,733 filed Oct. 5, 1978, which application is a continuation-in-part of application Ser. No. 852,899, filed Nov. 18, 1977, now abandoned. Generally, according to the process described in application Ser. No. 948,733 a vaporous mixture of 1,1,2-trichloroethane and a nonreactive diluent is fed to a reactor at a pressure of from 2 to 20 atmospheres, preferably from 4 to 10 atmospheres, the partial pressure of 1,1,2-trichloroethane in the vaporous mixture being preferably maintained at less than about 2.0 and most preferably at about 1.0 atmosphere although the 1,1,2-trichloroethane partial pressure could be maintained at sub-atmospheric levels. The vapor phase reaction is typically conducted at a temperature of at least about 375° C. and usually between 400° C. and 500° C., the contact time of the vaporous mixture with the catalyst in the reactor being not more than about two minutes and preferably not more than about 10 seconds. The catalyst may be used as a packed or fluidized bed. Although particle size is not particularly critical, for use as a packed bed, the catalyst particle size is typically in the range of 6 to 50 mesh (U.S. Sieve) and in the range of about 50 to 200 mesh (U.S. Sieve) for use as a fluidized bed.

The invention is further illustrated but is not intended to be limited by the following examples.

EXAMPLE 1

A quantity of silica gel (W. R. Grace & Co., Grade 40) having a particle size of 6 to 12 mesh (U.S. Sieve) and a surface area of about 700 square meters per gram was placed in a porcelain evaporating dish exposed to the atmosphere. A stream of ambient temperature (about 23° C.) compressed air saturated with water vapor by means of a bubbler assembly was directed into the mass of silica gel. The silica gel was periodically tested for adequacy of humidification by placing a sample in water at ambient temperature to determine the extent of disintegration. After four weeks contact with the water vapor laden air, the silica gel was determined to be adequately humidified according to the water contact test, i.e., the silica gel particles did not disintegrate when placed in liquid water.

About 142 grams of the humidified silica gel was placed in a one liter round bottom flask. About 16 grams of cesium nitrate ($CsNO_3$) was dissolved in 200 milliliters of warm water and added to the flask. The flask, containing the silica gel and cesium nitrate solution was rotated in a water bath maintained at about 55° C. for several hours until the cesium nitrate solution was absorbed by the silica gel. The contents of the flask were removed, placed in an oven, and dried overnight at 110° C., cooled to room temperature and stored for use. The catalyst contained about 10 percent by weight of cesium nitrate based on the combined weight of cesium nitrate and silica gel.

EXAMPLE 2

The procedure of Example 1 was followed except that 142 grams of humidified silica gel was treated with a solution of 16 grams of cesium carbonate ($Cs_2CO_3$) dissolved in 200 milliliters of water. The catalyst contained about 10 percent by weight of cesium carbonate based on the combined weight of cesium carbonate and silica gel.

EXAMPLE 3

The procedure of Example 1 was followed except that 142 grams of humidified silica gel was treated with a solution of 16 grams of cesium chloride (CsCl) dissolved in 200 milliliters of water. The catalyst contained about 10 percent by weight of cesium chloride based on the combined weight of cesium chloride and silica gel.

EXAMPLE 4

The procedure of Example 1 was followed except that 142 grams of humidified silica gel was treated with a solution containing 16.7 grams of cesium chloride (CsCl) and 8.4 grams of potassium fluoride (KF) dissolved in 200 milliliters of water. The catalyst contained about 10 percent by weight of cesium chloride and about 5.0 percent by weight of potassium fluoride based on the combined weight of cesium chloride, potassium fluoride and silica gel.

EXAMPLE 5

A vertical reactor was constructed from a 70 cm. length of 2.66 cm. I.D. Inconel ® 600 schedule 40 pipe. A preheater comprising a 30.5 cm. length of 2.66 cm. I.D. schedule 40 nickel pipe was joined at a right angle to and adjacent the upper end of the reactor pipe. The reactor was charged with the catalysts prepared in Examples 1 to 4 to a depth of about 25.4 cm., the catalyst bed supported on a porous silicon carbide disc mounted about 15.2 cm. from the lower end of the reactor pipe.

Heat was supplied to the reactor via a 30.5 cm. tube furnace disposed about that section of the reactor pipe containing the catalyst. The preheater was heated by a resistance heater made by covering the preheater pipe with a layer of glass cloth and wrapping there around a length of No. 22 nichrome wire.

The reactor and preheater were stabilized at operating temperature and liquid 1,1,2-trichloroethane was metered into the preheater wherein it was vaporized and the vaporized 1,1,2-trichloroethane was fed under super-atmospheric pressure downwardly through the particular catalyst bed and the emergent gas stream was collected and analyzed. Two runs were made with the cesium nitrate catalyst and one run each with the other catalyst. The results and conditions of these dehydrochlorination experiments are summarized in Table I.

As shown by the data in Table I, vapor phase dehydrochlorination of 1,1,2-trichloroethane in the presence of cesium nitrate results in greater catalytic selectivity to vinylidene chloride with higher product ratios of vinylidene chloride to 1,2-dichloroethylene isomers, as compared with other cesium-containing catalysts.

Although the invention has been described with reference to cesium nitrate and in particular to cesium nitrate supported on humidified, regular density silica gel, cesium nitrate may be unsupported or supported on other materials, e.g., silica, silica gels other than the regular density type, alumina, clay minerals, and the like. Moreover, other metal nitrates, e.g., potassium nitrate, sodium nitrate, rubidium nitrate and lithium nitrate are also believed to be suitable for use in the practice of this invention in its broadest aspects.

TABLE I

| Vapor Phase Dehydrochlorination of 1,1,2-Trichloroethane at Elevated Pressure With Cesium-Containing Catalysts | | | | | |
|---|---|---|---|---|---|
| Run No. | 1 | 2 | 3 | 4 | 5 |
| Reactor Temperature, °C. | 415 | 446 | 437 | 450 | 444 |
| Reactor Pressure, psig | 46 | 45 | 53 | 45 | 41 |
| Contact Time, seconds | 9 | 10 | 11 | 7 | 11 |
| Catalyst | $CsNO_3$ | $CsNO_3$ | $Cs_2CO_3$ | CsCl | CsCl-KF |
| TCE conversion, percent | 90 | 95 | 82 | 78 | 41 |
| Selectivity to VDC, percent | 39.8 | 41.0 | 37.9 | 34.4 | 36.1 |
| Selectivity to c-1,2, percent | 31.2 | 31.3 | 33.0 | 31.5 | 35.0 |

TABLE I-continued

| Vapor Phase Dehydrochlorination of 1,1,2-Trichloroethane at Elevated Pressure With Cesium-Containing Catalysts | | | | | |
|---|---|---|---|---|---|
| Selectivity to t-1,2, percent | 26.5 | 25.7 | 26.6 | 24.8 | 24.5 |
| Yield VDC/Pass, percent | 35.8 | 39.0 | 31.1 | 26.8 | 14.8 |
| Ratio VDC/c-,t-1,2 | 0.69 | 0.72 | 0.64 | 0.61 | 0.61 |

TCE = 1,1,2-trichloroethane
$CsNO_3$ = cesium nitrate
VDC = vinylidene chloride
$Cs_2CO_3$ = cesium carbonate
c-1,2 = cis,1,2-dichloroethylene
CsCl = cesium chloride
t-1,2 = trans-1,2-dichloroethylene
KF = potassium fluoride

I claim:

1. In a process for dehydrochlorinating 1,1,2-trichloroethane in the vapor phase and in the presence of a dehydrochlorination catalyst to produce vinylidene chloride, the improvement wherein cesium nitrate is used as the dehydrochlorination catalyst.

2. The improvement of claim 1 where in the cesium nitrate is supported on particulate, regular density silica gel, said silica gel, prior to being used as a support for the cesium nitrate, being humidified by exposing the silica gel to water vapor at a temperature between 5° C. and 50° C. for a time sufficient such that there will be no significant disintegration of the silica gel upon its being contacted with liquid water at ambient temperature.

3. The improvement of claim 2 wherein the silica gel has a surface area of at least 500 square meters per gram, an average pore diameter of between 10 and 100 angstroms and a silica content of at least 99.5 percent by weight on an anhydrous basis.

4. The improvement of claim 2 wherein the cesium nitrate content of the catalyst is from about 0.5 to 25 percent by weight based on the combined weight of cesium nitrate and silica gel.

5. The improvement of claim 4 wherein the cesium nitrate content of the catalyst is from about 5 to 15 percent by weight based on the combined weight of cesium nitrate and silica gel.

6. The improvement of claim 2 wherein the silica gel particle size is in the range of from 6 to 200 mesh.

* * * * *